United States Patent
Patel et al.

(10) Patent No.: US 11,224,459 B2
(45) Date of Patent: Jan. 18, 2022

(54) ATHERECTOMY CATHETER WITH SHAPEABLE DISTAL TIP

(71) Applicant: AVINGER, INC., Redwood City, CA (US)

(72) Inventors: Himanshu N. Patel, San Jose, CA (US); Anthony J. Fernandez, San Mateo, CA (US); Vincent Yeh, Redwood City, CA (US)

(73) Assignee: Avinger, Inc., Redwood City, CA (US)

( * ) Notice: Subject to any disclaimer, the term of this patent is extended or adjusted under 35 U.S.C. 154(b) by 78 days.

(21) Appl. No.: 16/310,470

(22) PCT Filed: Jun. 30, 2017

(86) PCT No.: PCT/US2017/040431
§ 371 (c)(1),
(2) Date: Dec. 17, 2018

(87) PCT Pub. No.: WO2018/006041
PCT Pub. Date: Jan. 4, 2018

(65) Prior Publication Data
US 2019/0209206 A1    Jul. 11, 2019

Related U.S. Application Data

(60) Provisional application No. 62/357,173, filed on Jun. 30, 2016.

(51) Int. Cl.
*A61B 17/3207*    (2006.01)
*A61D 1/02*    (2006.01)
(Continued)

(52) U.S. Cl.
CPC ........ *A61B 17/320783* (2013.01); *A61D 1/02* (2013.01); *A61B 2017/00309* (2013.01);
(Continued)

(58) Field of Classification Search
CPC .. A61B 17/320783; A61B 2017/00309; A61B 2017/00331; A61B 2107/00738;
(Continued)

(56) References Cited

U.S. PATENT DOCUMENTS

| 3,367,727 A | 2/1968 | Ward et al. |
| 3,908,637 A | 9/1975 | Doroshow |

(Continued)

FOREIGN PATENT DOCUMENTS

| CN | 1875242 A | 12/2006 |
| CN | 1947652 A | 4/2007 |

(Continued)

OTHER PUBLICATIONS

Choma et al.; Sensitivity advantage of swept source and fourier domain optical coherence tomography; Optics Express; 11(18); pp. 2183-2189; Sep. 8, 2003.

(Continued)

*Primary Examiner* — Richard G Louis
(74) *Attorney, Agent, or Firm* — Shay Glenn LLP

(57) ABSTRACT

An atherectomy catheter for use in a vessel includes an elongate catheter body and an annular cutter. The elongate catheter body includes a fixed jog section with a pre-set curvature and a flexible section that has a greater flexibility than a remainder of the elongate catheter body. The fixed jog section and flexible section are formed of a frame including a plurality of circumferential slits therein. Also described herein is an atherectomy catheter for use in a vessel includes an elongate catheter body, an annular cutter, and an s-shaped curved portion in the elongate catheter body. The curved portion includes a frame having a longitudinal proximal spine and a longitudinal distal spine. The longitudinal proximal spine is positioned approximately 180 degrees away from the longitudinal distal spine.

28 Claims, 19 Drawing Sheets

(51) Int. Cl.
*A61B 17/00* (2006.01)
*A61M 25/00* (2006.01)
*A61M 25/01* (2006.01)

(52) U.S. Cl.
CPC .............. *A61B 2017/00331* (2013.01); *A61B 2017/00738* (2013.01); *A61B 2017/320791* (2013.01); *A61M 25/0054* (2013.01); *A61M 25/0138* (2013.01)

(58) Field of Classification Search
CPC ......... A61B 2017/320791; A61D 1/02; A61M 25/0054; A61M 25/0138
See application file for complete search history.

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,429,136 A | 7/1995 | Milo et al. |
| 5,431,673 A | 7/1995 | Summers et al. |
| 5,437,284 A | 8/1995 | Trimble |
| 5,459,570 A | 10/1995 | Swanson et al. |
| 5,460,168 A | 10/1995 | Masubuchi et al. |
| 5,465,147 A | 11/1995 | Swanson |
| 5,507,760 A | 4/1996 | Wynne et al. |
| 5,507,795 A | 4/1996 | Chiang et al. |
| 5,517,998 A | 5/1996 | Madison |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |

(56) References Cited

U.S. PATENT DOCUMENTS

| | | |
|---|---|---|
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1* | 8/2004 | Simpson ............ A61B 5/0084 606/159 |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1* | 9/2004 | Griffin ............ A61M 25/0051 604/524 |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |

(56) References Cited

U.S. PATENT DOCUMENTS

| | | |
|---|---|---|
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1* | 4/2010 | Honeck ............. A61M 25/0668 604/246 |
| 2010/0125253 A1 | 5/2010 | Olson |
| 2010/0130996 A1 | 5/2010 | Doud et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |

(56) References Cited

U.S. PATENT DOCUMENTS

| | | |
|---|---|---|
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0238869 A1 | 9/2012 | Schmitt et al. |
| 2012/0259337 A1 | 10/2012 | Del Rio et al. |
| 2012/0277730 A1* | 11/2012 | Salahieh ............ A61M 25/0138 604/527 |
| 2012/0289971 A1 | 11/2012 | Segermark et al. |
| 2013/0035692 A1 | 2/2013 | Sorensen et al. |
| 2013/0072787 A1 | 3/2013 | Wallace et al. |
| 2013/0096589 A1 | 4/2013 | Spencer et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0296695 A1 | 11/2013 | Spencer et al. |
| 2013/0317519 A1 | 11/2013 | Romo et al. |
| 2013/0325003 A1 | 12/2013 | Kapur et al. |
| 2014/0005534 A1 | 1/2014 | He et al. |
| 2014/0046250 A1* | 2/2014 | Jain .................... A61M 25/0138 604/95.03 |
| 2014/0128893 A1 | 5/2014 | Guggenheimer et al. |
| 2014/0187949 A1 | 7/2014 | Zhao et al. |
| 2014/0222042 A1 | 8/2014 | Kessler et al. |
| 2014/0222047 A1 | 8/2014 | Vreeman |
| 2014/0275996 A1 | 9/2014 | Stigall |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0141816 A1* | 5/2015 | Gupta ................ A61B 5/0066 600/427 |
| 2015/0146211 A1 | 5/2015 | Bhagavatula et al. |
| 2015/0164530 A1 | 6/2015 | Carver et al. |
| 2015/0320975 A1 | 11/2015 | Simpson et al. |
| 2016/0008025 A1 | 1/2016 | Gupta et al. |
| 2016/0038030 A1 | 2/2016 | Smith et al. |
| 2016/0144155 A1 | 5/2016 | Simpson et al. |
| 2016/0262791 A1 | 9/2016 | Patel et al. |
| 2016/0262839 A1 | 9/2016 | Spencer et al. |
| 2016/0310700 A1 | 10/2016 | Drake et al. |
| 2016/0338582 A1 | 11/2016 | Tachibana et al. |
| 2016/0354109 A1 | 12/2016 | Guggenheimer et al. |
| 2016/0354110 A1 | 12/2016 | Guggenheimer et al. |
| 2017/0065295 A1 | 3/2017 | Patel et al. |
| 2017/0172666 A1 | 6/2017 | Govari et al. |
| 2017/0238803 A1 | 8/2017 | Kankaria |
| 2017/0238808 A1 | 8/2017 | Simpson et al. |
| 2017/0273711 A1 | 9/2017 | Simpson et al. |
| 2018/0042520 A1 | 2/2018 | Patel et al. |
| 2018/0049700 A1 | 2/2018 | Black et al. |
| 2018/0146978 A1 | 5/2018 | Patel et al. |
| 2018/0192880 A1 | 7/2018 | Patel et al. |
| 2018/0207417 A1 | 7/2018 | Zung et al. |
| 2018/0256039 A1 | 9/2018 | Smith et al. |
| 2018/0256187 A1 | 9/2018 | Patel et al. |
| 2018/0364024 A1 | 12/2018 | Baca et al. |
| 2018/0368688 A9 | 12/2018 | Simpson et al. |
| 2021/0059713 A1 | 3/2021 | Patel et al. |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| EP | 2942028 A1 | 11/2015 |
| JP | S62-275425 A | 11/1987 |
| JP | 03502060 A | 2/1990 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |

(56) References Cited

FOREIGN PATENT DOCUMENTS

| WO | WO2009/023635 A1 | 2/2009 |
|----|------------------|--------|
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |
| WO | WO2015/074018 A1 | 5/2015 |
| WO | WO2015/101747 A1 | 7/2015 |
| WO | WO2015/120146 A1 | 8/2015 |
| WO | WO2015/165736 A1 | 11/2015 |
| WO | WO2017/007853 A1 | 1/2017 |
| WO | WO2017/132247 A1 | 8/2017 |
| WO | WO2018/094041 A1 | 5/2018 |

OTHER PUBLICATIONS

De Boer et al.; Improved signal-to-noise ratio in spectral-domain compared with time-domain optical coherence tomography; Optics Letters; 28(21); pp. 2067-2069; Nov. 2003.

Leitgeb et al.; Performance of fourier domain vs time domain optical coherence tomography; Optics Express; 11(8); pp. 889-894; Apr. 21, 2003.

Rollins et al.; Optimal interferometer designs for optical coherence tomography; Optics Letters; 24(21); pp. 1484-1486; Nov. 1999.

Tachibana et al.; U.S. Appl. No. 16/372,112 entitled "Atherectomy catheter drive assemblies," filed Apr. 1, 2019.

Radjabi et al.; U.S. Appl. No. 16/347,840 entitled "Methods, systems and apparatuses for displaying real-time catheter position," filed May 7, 2019.

Stamper et al.; Plague characterization with optical coherence tomography. Journal of the American College of Cardiology. 47(8); pp. 69-79; Apr. 18, 2006.

Patel et al.; U.S. Appl. No. 16/681,807 entitled "Atherectomy catheters and occlusion crossing devices," filed Nov. 12, 2019.

Bayer Material Science: ; Snap-Fit Joints for Plastics; 26 pages; retrieved from the Internet: ( https:web.archive.org/web/20121119232733if_/http://fab.cba.mit.edu.80/classes/S62.12/people/vernelle.noel/Plastic_Snap_fit_design.pdf) on Sep. 26, 2018.

Schmitt et al.; A new rotational thrombectomy catheter: System design and first clinical esperiences; Cardiovascular and Interventional Radiology; Sprinver-Verlag; 22(6); pp. 504-509; Nov. 1, 1999.

Patel et al.; U.S. Appl. No. 16/801,047 entitled "Micro-molded anamorphic reflector lens for image guided therapeutic/diagnostic catheters," filed Feb. 25, 2020.

Aziz et al.; Chronic total occlusions—a stiff challege requiring a major breakthrough: is there light at the end of the tunnel?; Heart; vol. 91; suppl. III; pp. 42-48; Jun. 2005.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; Cleo, May 4, 2008; 2 pages.

Linares et al.; Arbitrary single-mode coupling by tapered and nontapered grin fiber lenses; Applied Optics; vol. 29; No. 28; pp. 4003-4007; Oct. 1, 1990.

Muller et al.; Time-gated infrared fourier-domain optical coherence tomography; CFM5; San Jose, California; Cleo May 4, 2008; 2 pages.

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.

Wang et al.; Common-path endoscopic Fourier domain OCT with a reference Michelson interferometer; Proceedings of the SPIE; vol. 7566; p. 75660L-75660L-7; Jan. 2010.

Newhauser et al.; U.S. Appl. No. 15/954,407 entitled "Occlusion-crossing devices," filed Apr. 16, 2018.

Christensen; U.S. Appl. No. 16/069,545 entitled "OCT imaging catheter with lag correction," filed Jul. 12, 2018.

Rosenthal et al.; U.S. Appl. No. 16/105,743 entitled "Atherectomy catheter with laterally-displaceable tip," filed Aug. 20, 2018.

Patel et al.; U.S. Appl. No. 16/148,246 entitled "Atherectomy catheter with serrated cutter," filed Oct. 1, 2018.

Simpson et al.; U.S. Appl. No. 16/194,183 entitled "Indetification of elastic lamina to guide interventional therapy," filed Nov. 16, 2018.

Fernandez et al., U.S. Appl. No. 16/305,136 entitled "Catheter device with detachable distal end," filed Nov. 28, 2018.

Patel et al.; U.S. Appl. No. 16/490,903 entitled "Atherctomy catheter," filed Jul. 2, 2019.

Black et al.; U.S. Appl. No. 16/506,851 entitled "Optical coherence tomography for biological imaging," filed Jul. 9, 2019.

Patel et al.; U.S. Appl. No. 16/516,093 entitled "High speed chronic total occlusion crossing devices," filed Jul. 18, 2019.

Sharma et al.; Common-path optical coherence tomography with side-viewing bare fiber probe for endoscopic optical coherence tomography; vol. 78; 113102; 5 pages; Nov. 6, 2007.

Smith et al.; U.S. Appl. No. 16/941,310 entitled "Chronic total occlusion crossing devices with imaging," filed Jul. 28, 2020.

Spencer et al.; U.S. Appl. No. 16/943,446 entitled "Catheter-based off-axis optical coherence tomography imaging system," filed Jul. 30, 2020.

Simpson et al.; U.S. Appl. No. 17/075,548 entitled "Identification of elastic lamina to guide interventional therapy," filed Oct. 20, 2020.

Merriam Webster; Proximal (Definition); 10 pages; retrieved from the internet (https://www.merriam-webster.com/dictionary/proximal) on Jun. 9, 2021.

Wikipedia; Hinge; 4 pages; retrieved from the internet (https://en.wikipedia.org/w/index.php?title=Hinge&oldid=479569345) on Jun. 9, 2021.

Smith et al.; U.S. Appl. No. 17/189,123 entitled "Optical pressure sensor assembly," filed Mar. 1, 2021.

Kankaria; U.S. Appl. No. 17/209,162 entitled "Optical coherence tomography with graded index fiber for biological imaging," filed Mar. 22, 2021.

Newhauser et al.; U.S. Appl. No. 17/209,168 entitled "Occlusion-crossing devices," filed Mar. 22, 2021.

* cited by examiner

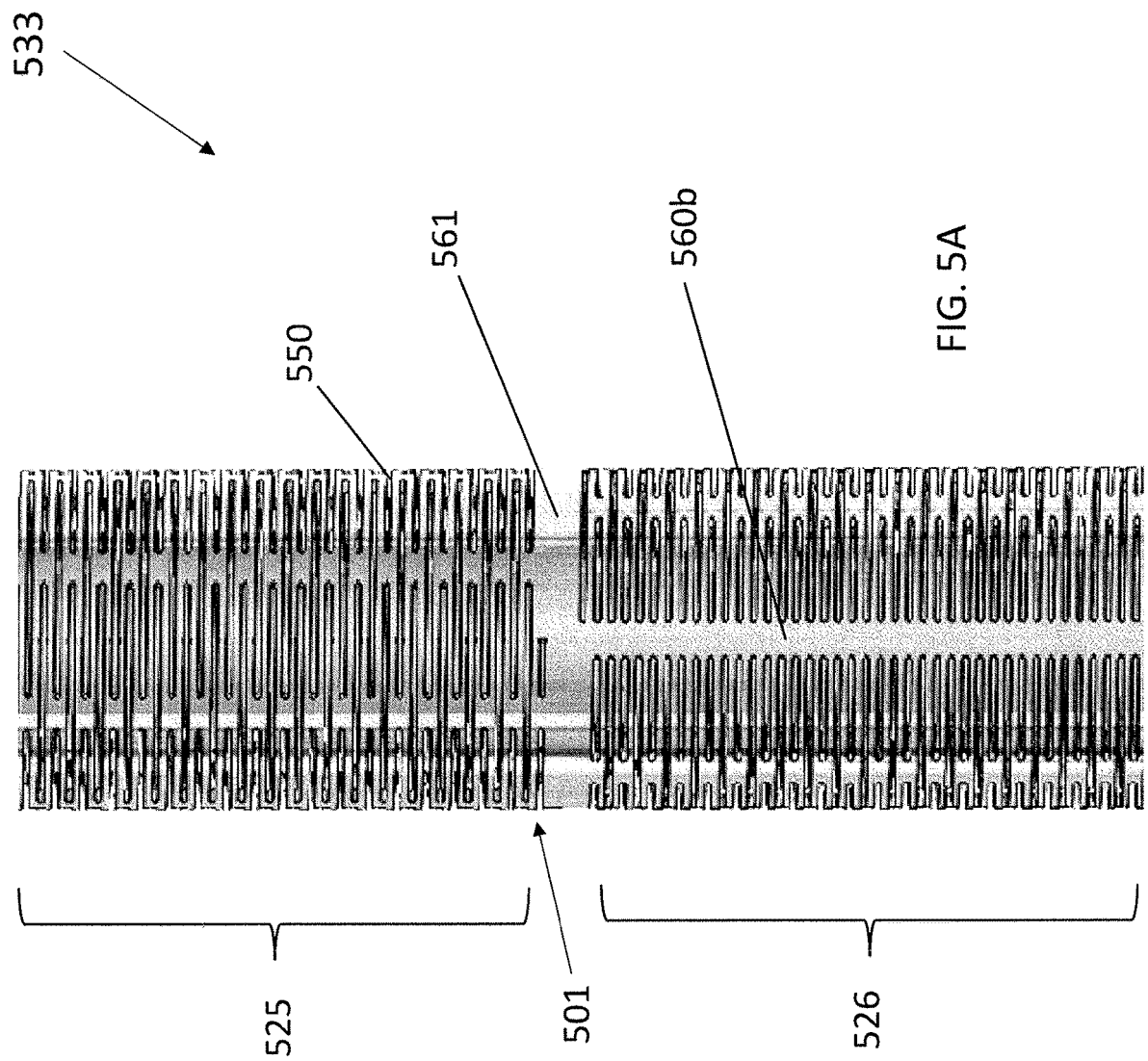

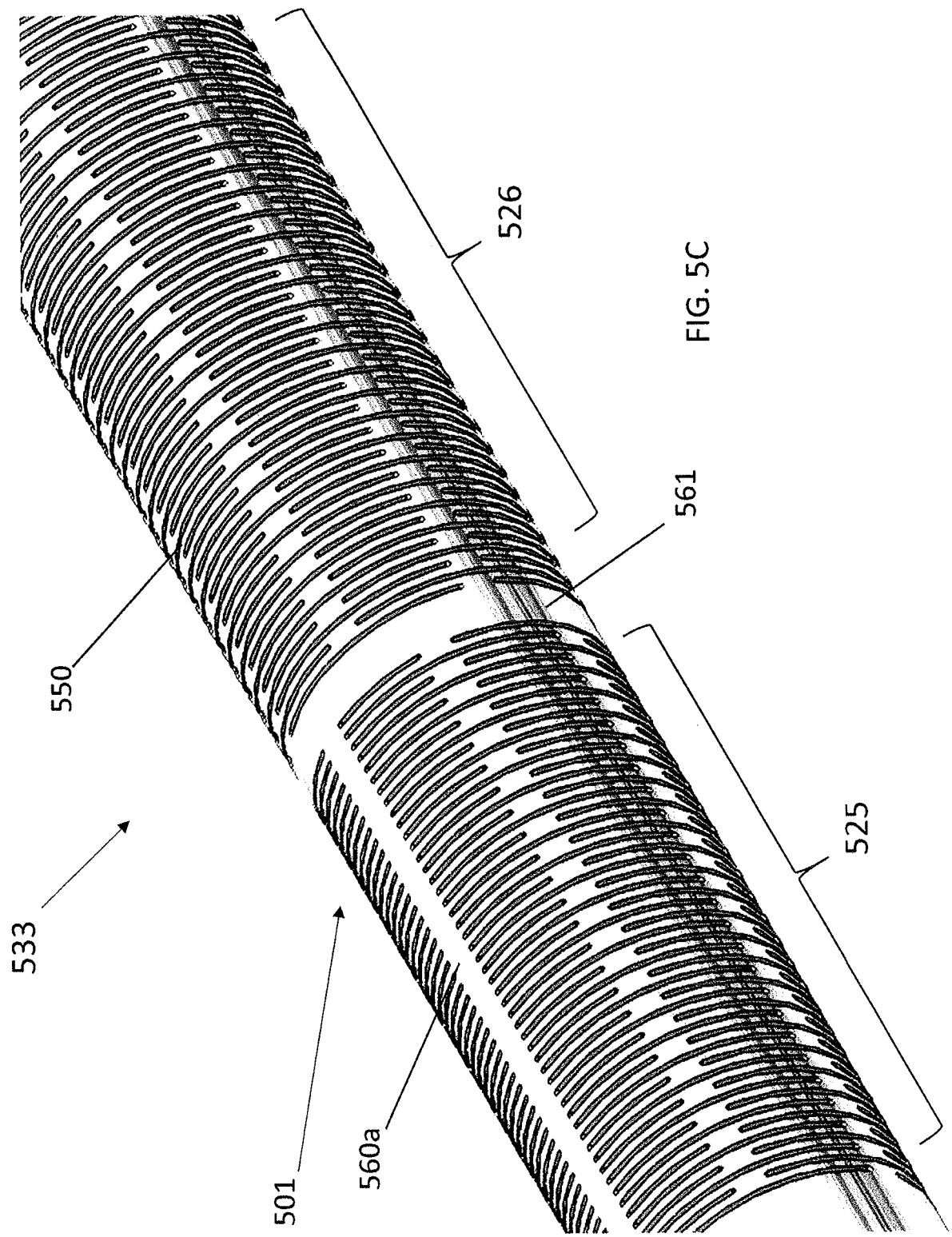

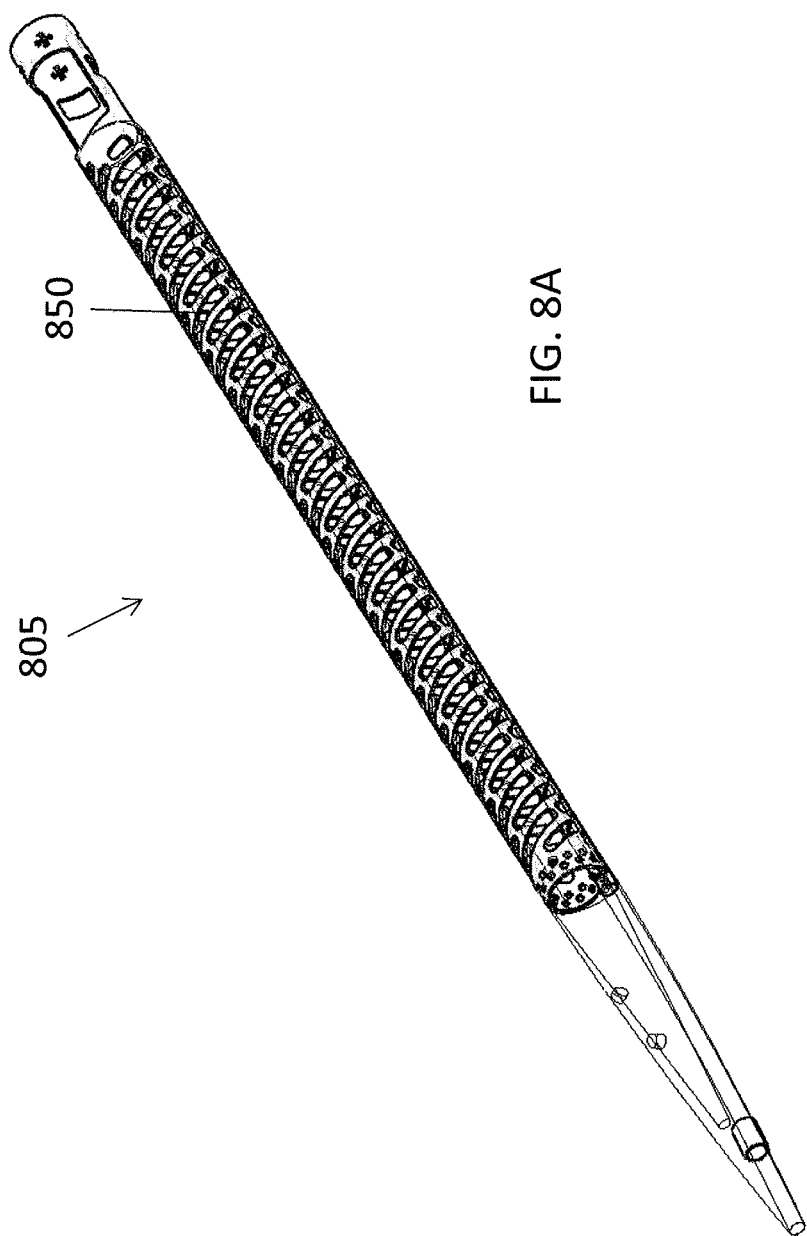

ATHERECTOMY CATHETER WITH SHAPEABLE DISTAL TIP

CROSS REFERENCE TO RELATED APPLICATIONS

This application claims priority to U.S. Provisional Patent Application No. 62/357,173, filed Jun. 30, 2016, and titled "ATHERECTOMY CATHETER WITH SHAPEABLE DISTAL TIP," which is herein incorporated by reference in its entirety.

This application may also be related to U.S. Publication No. 20150141816, titled "ATHERECTOMY CATHETER WITH IMAGING," filed on Mar. 15, 2013, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are devices for treatment of an occluded body lumen, such as for the removal of occlusive materials from blood vessels. In particular, described herein are atherectomy catheters that are adapted to easily maneuver against tissue and plaque buildup within vessels for debulking.

BACKGROUND

Atherosclerosis is disease in which accumulation of atheromatous materials builds up inside a person's arteries. Atherosclerosis occurs as part of the natural aging process, but may also occur due to a person's diet, hypertension, vascular injury, heredity, and so forth. Atherosclerosis can affect any artery in the body, including arteries in the heart, brain, arms, legs, pelvis, and kidneys. Atherosclerosis deposits may vary in their properties as well. Some deposits are relatively soft, other types may be fibrous, some are calcified, or a combination of all three. Based on the location of the plaque accumulation, different diseases may develop. For example, coronary heart disease occurs when plaque builds up in the coronary arteries, which supply oxygenated blood to the heart. If plaque buildup blocks the carotid artery, arteries located on each side of the neck that supply oxygen to the brain, a stroke may be the result.

Atherosclerosis may be treated in a number of ways including medication, bypass surgery, and catheter-based approaches. Atherectomy procedures involve excising or dislodging materials that block a blood vessel. Many atherectomy catheters typically have a substantially straight central axis. However, atherectomy catheters having a straight profile may be difficult to maneuver close enough to the inner surface of the arterial walls to remove all plaque buildup. Moreover, plaque removal can be complicated with such straight profile catheters when plaque formations accumulate in the curves and more tortuous portions of an artery.

The atherectomy catheters described herein address some of these challenges.

SUMMARY OF THE DISCLOSURE

In general, in one embodiment, an atherectomy catheter for use in a vessel includes an elongate catheter body and an annular cutter. The elongate catheter body includes a fixed jog section with a pre-set curvature and a flexible section that has a greater flexibility than a remainder of the elongate catheter body. The fixed jog section and flexible section are formed of a frame including a plurality of circumferential slits therein.

This and other embodiments can include one or more of the following features. The frame in the fixed jog section can further include a longitudinal spine extending therethrough that does not have slits. The atherectomy catheter can further include a cutting window through which the annular cutter extends. The cutting window can be positioned distal of the fixed jog section and the flexible section so as to urge the cutter into the vessel. The atherectomy catheter can further include at least one laminating layer positioned over or under the frame of the fixed jog section. The laminating layer can be made of a polymer. The frame can be made of metal. The plurality of circumferential slits can be arranged in a repeating pattern. The fixed jog section can form an angle of 130° to 160° in the elongate catheter body. The frame can further include an annular spine without slits that extends between the fixed jog section and the flexible section. The flexible section can be configured to passively bend to angles of 130°-160°.

In general, in one embodiment, an atherectomy catheter for use in a vessel includes an elongate catheter body, an annular cutter, and an s-shaped curved portion in the elongate catheter body. The curved portion includes a frame having a plurality of annular spines connected together by a longitudinal proximal spine and a longitudinal distal spine. The longitudinal proximal spine is positioned approximately 180 degrees away from the longitudinal distal spine.

This and other embodiments can include one or more of the following features. The plurality of annular spines can include a first annular spine, a second annular spine, and a third annular spine. The longitudinal proximal spine can connect the first annular spine and the second annular spine, and the longitudinal distal spine can connect the second annular spine and the third annular spine. The atherectomy catheter can further include a cutting window through which the annular cutter extends. The cutting window can be positioned distal of the curved portion and on an outer circumference of the s-shaped curve so as to urge the cutter into the vessel. The s-shaped curved portion can be configured to be activated by pulling or pushing on a shaft of the atherectomy catheter. The atherectomy catheter can further include at least one laminating layer positioned over or under the frame. The laminating layer can be made of a polymer. The frame can be made of metal. The distal longitudinal spine can be positioned adjacent to an exposed portion of the cutter. The distal longitudinal spine can be on a same side of the elongate catheter body as the exposed portion of the cutter. The longitudinal proximal spine can form a first angle, and the longitudinal distal spine can form a second angle. The first and second angles can extend in opposite directions, and the first angle can be between 140 and 160 degrees and the second angle can be between 140 and 160 degrees. A distal-most spine of the plurality of spines can include a beveled distal edge. The atherectomy catheter can further include a nosecone configured to pivot away from the elongate body to expose the cutter. The bevel can be configured to provide space for the nosecone to pivot.

In general, in one embodiment, an atherectomy catheter for use in a vessel includes an elongate catheter body, an annular cutter, and an s-shaped curved portion in the elongate catheter body. The curved portion includes a frame having a proximal section and a distal section. The proximal section has a plurality of circumferential proximal slits and a longitudinal proximal spine without slits, and the distal section having a plurality of circumferential distal slits and a longitudinal distal spine without slits. The longitudinal proximal spine is positioned approximately 180 degrees away from the longitudinal distal spine.

This and other embodiments can include one or more of the following features. The atherectomy catheter can further include a cutting window through which the annular cutter extends. The cutting window can be positioned distal of the distal section and on an outer circumference of the s-shaped curve so as to urge the cutter into the vessel. The s-shaped curved portion can be configured to be activated by pulling or pushing on a shaft of the atherectomy catheter. The atherectomy catheter can further include at least one laminating layer positioned over or under the frame. The laminating layer can be made of a polymer. The frame can be made of metal. The plurality of circumferential proximal slits can be arranged in a first repeating pattern, and the plurality of circumferential distal slits can be arranged in a second repeating pattern. The first repeating pattern and the second repeating pattern can be circumferentially offset from one another. The distal longitudinal spine can be positioned adjacent to an exposed portion of the cutter. The distal longitudinal spine can be on a same side of the elongate catheter body as the exposed portion of the cutter. The proximal section can form a first angle, and the distal section forms a second angle. The first and second angles can extend in opposite directions, and the first angle can be between 140 and 160 degrees and the second angle can be between 140 and 160 degrees. The frame can further include an annular spine without slits extending between the proximal section and the distal section.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 5A is a top view of a user-activated curved portion of an atherectomy catheter.

FIGS. 5B and 5C are perspective views of the curved portion of FIG. 5A.

FIG. 8A shows an exemplary flexible nosecone for use with an atherectomy catheter.

DETAILED DESCRIPTION

Described herein is an atherectomy catheter having an elongate body with a curved distal portion, a nosecone and a rotatable annular cutter. The curved portion (which can otherwise be called a bent/bendable portion or jog mechanism) can advantageously be used to push the cutter up against the vessel wall to enhance the efficiency of cutting.

Figure 1A:
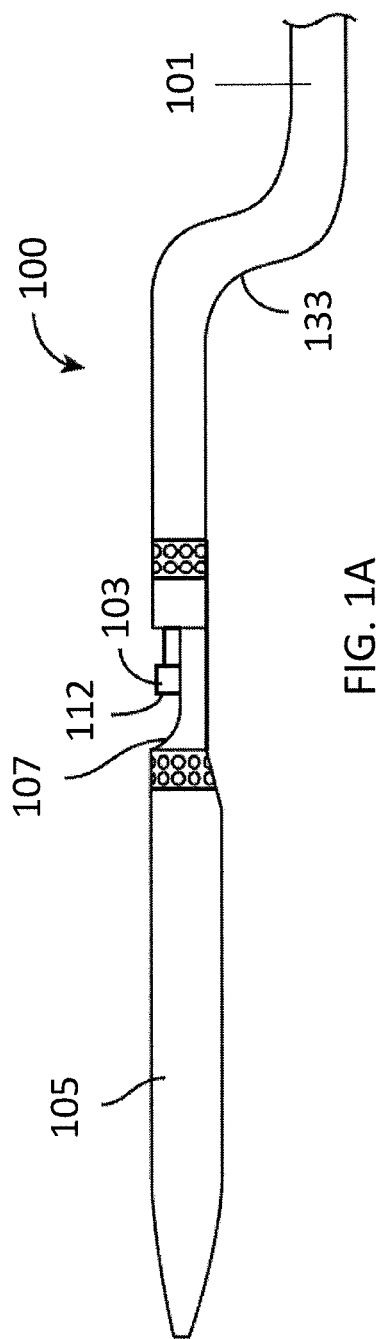
FIG. 1A shows an atherectomy catheter having a fixed jog.
Figure 1B:
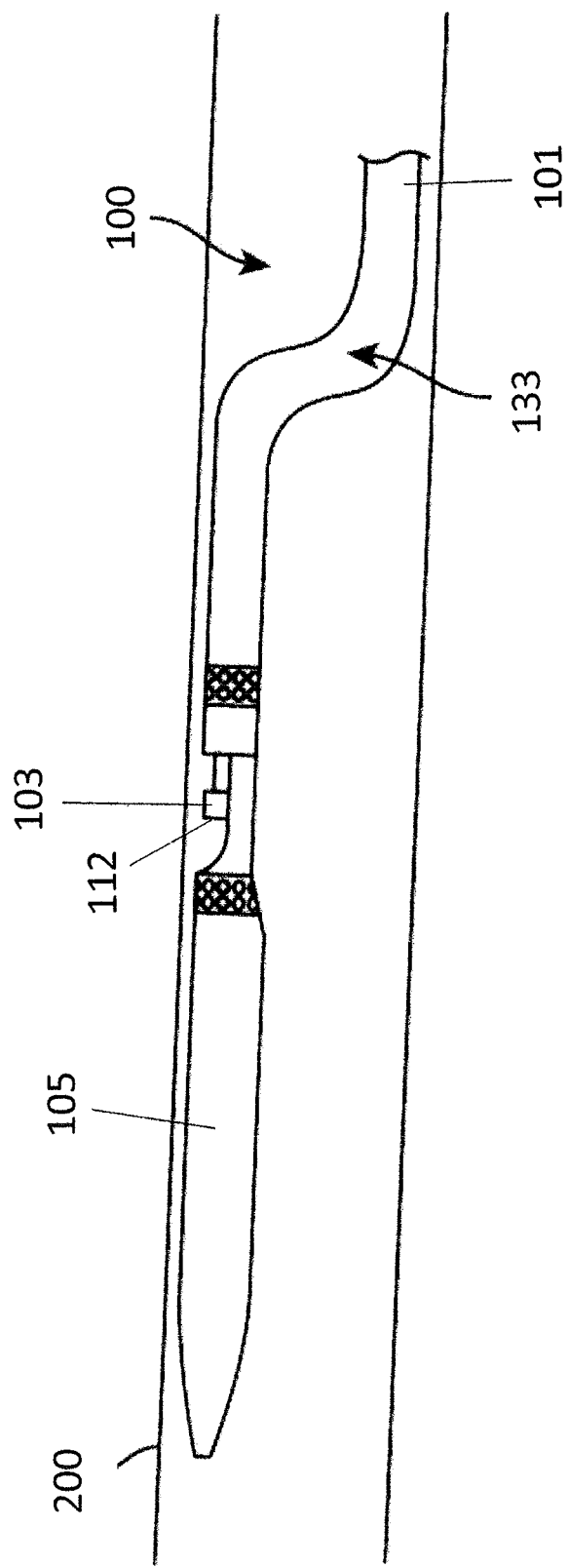
FIG. 1B shows the atherectomy catheter of FIG. 1A in a vessel.
Figure 2:
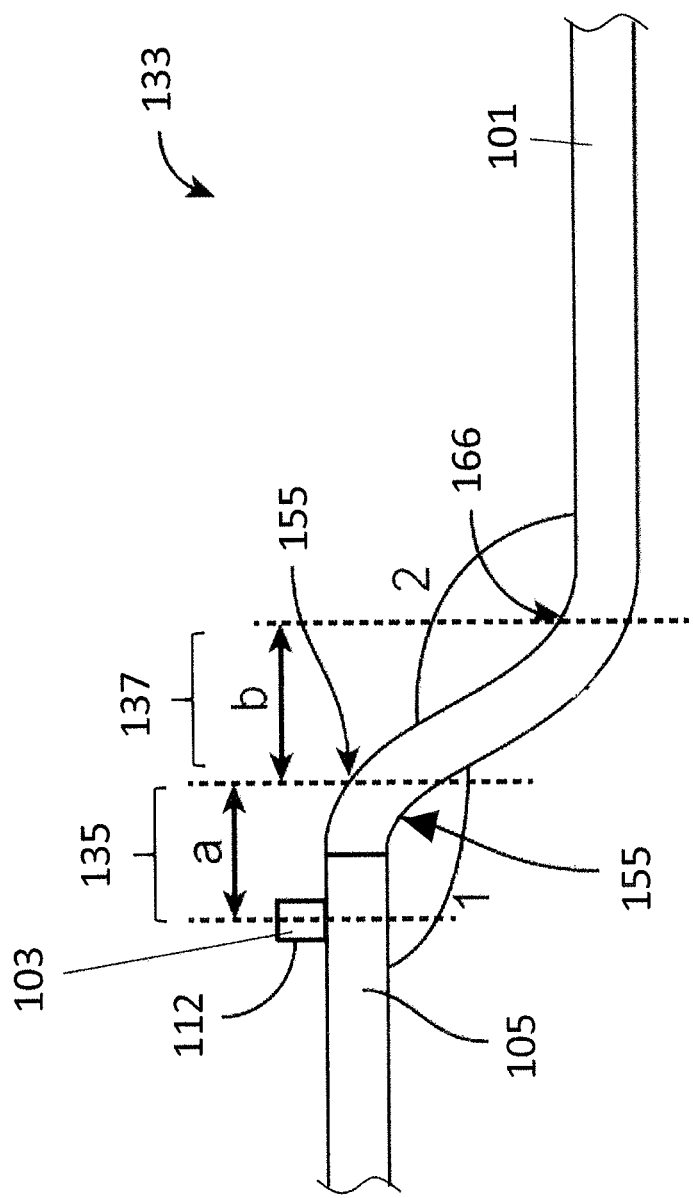
FIG. 2 shows a drawing of the atherectomy catheter of FIG. 1A with relative angles and dimensions.

FIGS. 1A and 1B show an exemplary atherectomy catheter 100 having a curved portion along the elongate catheter body. Referring to FIGS. 1A-2, the atherectomy catheter 100 can include a catheter body 101 with a curved portion 133, a rotatable annular cutter 103 at a distal end of the catheter body 101, and a nosecone 105 at a distal end of the catheter body 101. The nosecone 105 can include a cutting window 107 configured to allow the cutter 103 to cut therethrough. The catheter 101 can further include a curved portion 133 in the catheter body 101 to radially push the cutter 103 against the vessel wall.

The curved portion 133 can be a fixed jog (i.e., have a pre-set shape). Further, the curved portion can be curved or bent such that the cutting window 107 is on the radially outermost portion of the curved portion 133 (thereby allowing the cutting window 107 to be urged against a vessel wall in use). In one embodiment, the curved portion 133 can be pre-formed, for example, by using pre-deflected shaped-set nitinol ribbon segments embedded in the outer shaft. The curved portion 133 can have two inflection points 155, 166 of opposite curvature (i.e., one curving up and the other curving down) so as to form an approximate "s" shape. In one embodiment, the s-shape can be configured such that a distal end of the catheter body 101 is offset from, but substantially parallel to, a proximal end of the catheter body 101. In other embodiments, the distal end and proximal ends of the catheter body 101 can be at a slight angle to one another so as to control the angle of cutter engagement with the vessel wall.

Thus, as shown in FIG. 2, the "s-shape" of the curved portion 133 can include a proximal section 137 have a length b that extends from the center of the distal inflection point 155 to the center of the proximal inflection point 166. Further, the curved portion 133 can include a distal section 135 having a length a that extends from the cutting edge 112 to the center of the distal inflection point 155. Further, there can be distal angle 1 at the distal end of the "s-shape" and a proximal angle 2 at the proximal end of the "s-shape." These lengths (a, b) and angles (1, 2) can be tuned to achieve the desired jog or offset in order to obtain optimum apposition to tissue walls. For example, the length a can be shorter than the length b to ensure that the cutter is as close to the angle 1 as possible, thereby providing better apposition of the cutter 303. The angles 1 and 2 can be between 120 and 180 degrees, such as between 140 and 160 degrees. In one example, the length a is between 5 and 10 mm, the length b is between 10 and 15 mm, the angle 1 is 140 degrees and angle 2 is 160 degrees for a catheter configured to be used in a vessel having a 2.5-4 mm diameter.

The curved portion 133 can advantageously radially push the distal end of the catheter against a vessel wall 200, thereby enabling optimized cutting and/or imaging of the vessel as shown in FIG. 1B.

Figure 3A:
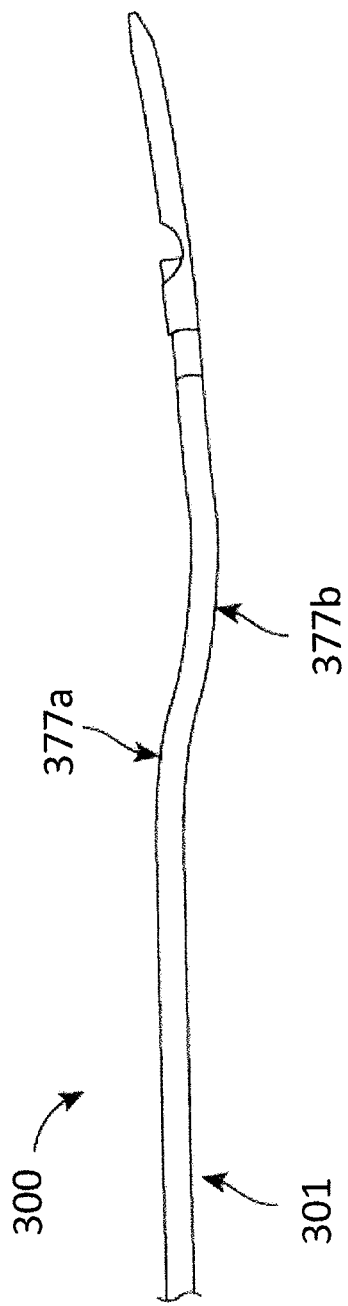
FIG. 3A shows a variation of a distal end of an atherectomy catheter that includes a user-activated curved portion with stiffening members that cause the catheter to deform to a predetermined curved configuration when activated.
Figure 3B:
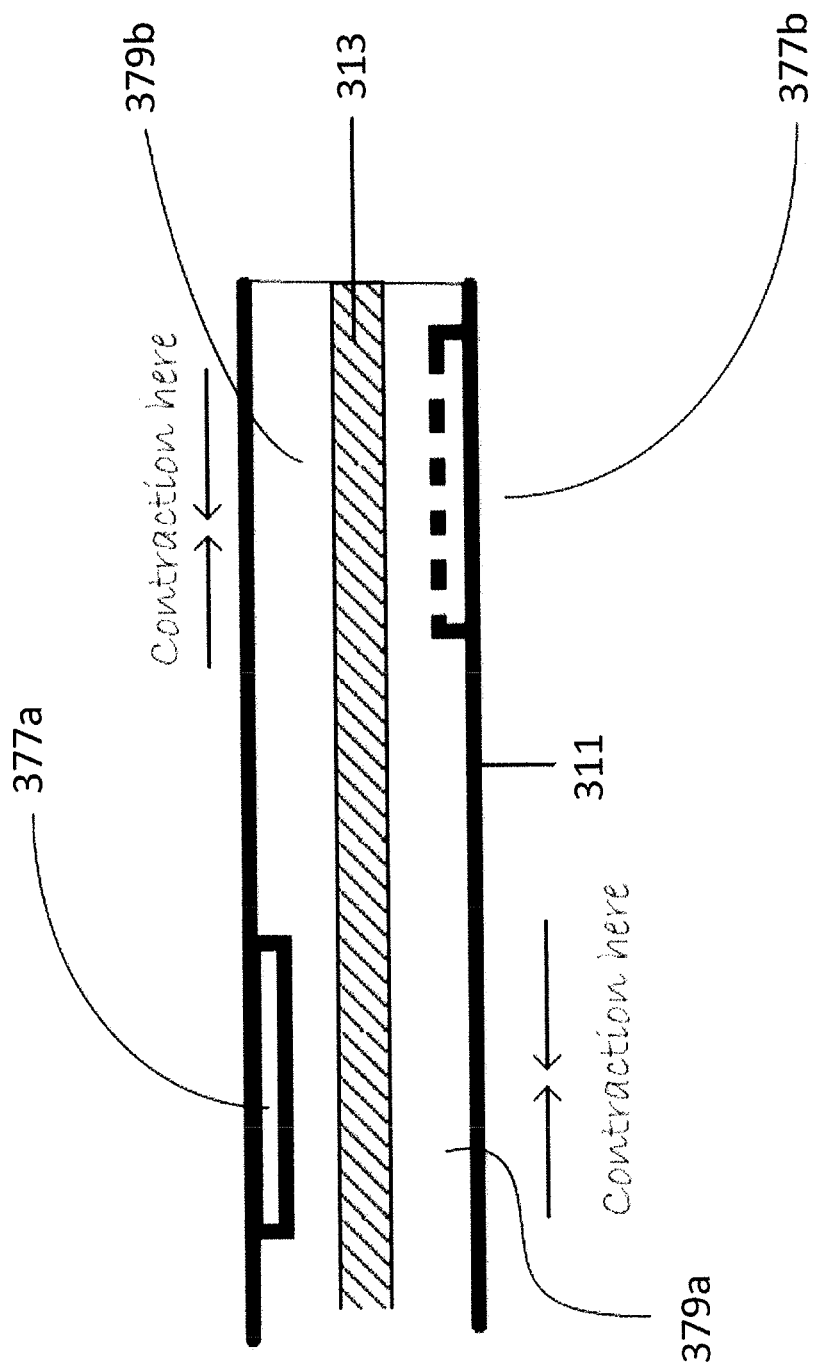
FIG. 3B is a schematic showing the stiffening members of the atherectomy catheter of FIG. 3A.

FIGS. 3A-3B show another embodiment of an exemplary catheter 300 that includes a curved portion 333 in the catheter body that urges the atherectomy cutter against the vessel wall. The curved portion 333 can have similar dimensions and features as curved portion 133. In contrast to the fixed jog curved portion 133 of catheter 100, however, the curved portion 333 can be a user-activated jog. Thus, referring to FIGS. 3A and 3B, the catheter 300, can be de-deflected into a curved portion 333 by tensile and compressive interaction between an inner shaft 313 (which can be a drive shaft for a cutter) and outer shaft 311 that are fixed together at the distal end but free to move relative to one another at the proximal end. The outer shaft 311 can include stiffening members 377a,b, such as nitinol or stainless steel, stiffening members, configured to bias the deflection to a set shape. As shown in FIG. 3B, there can be two stiffening members 377a, 377b that can be axially aligned with the outer shaft 311 and axially and radially offset from one another. As a result, when compression is applied on the outer shaft 311 (such as by pulling on the inner shaft 313 or a separate pullwire or shaft), the portions 379a,b of the outer shaft opposite to the stiffening members 377a,b will contract. The contraction of the two portions 379a, 379b will result in an s-shape similar to the catheter 100 shown in FIG. 1. As a result, the catheter will deflect into jog or s-shaped configuration where the distal end of the shaft is offset and parallel to the main shaft body. It is to be understood that other numbers and arrangements of stiffening members are possible, as are other resulting jog shapes.

Figure 4A:
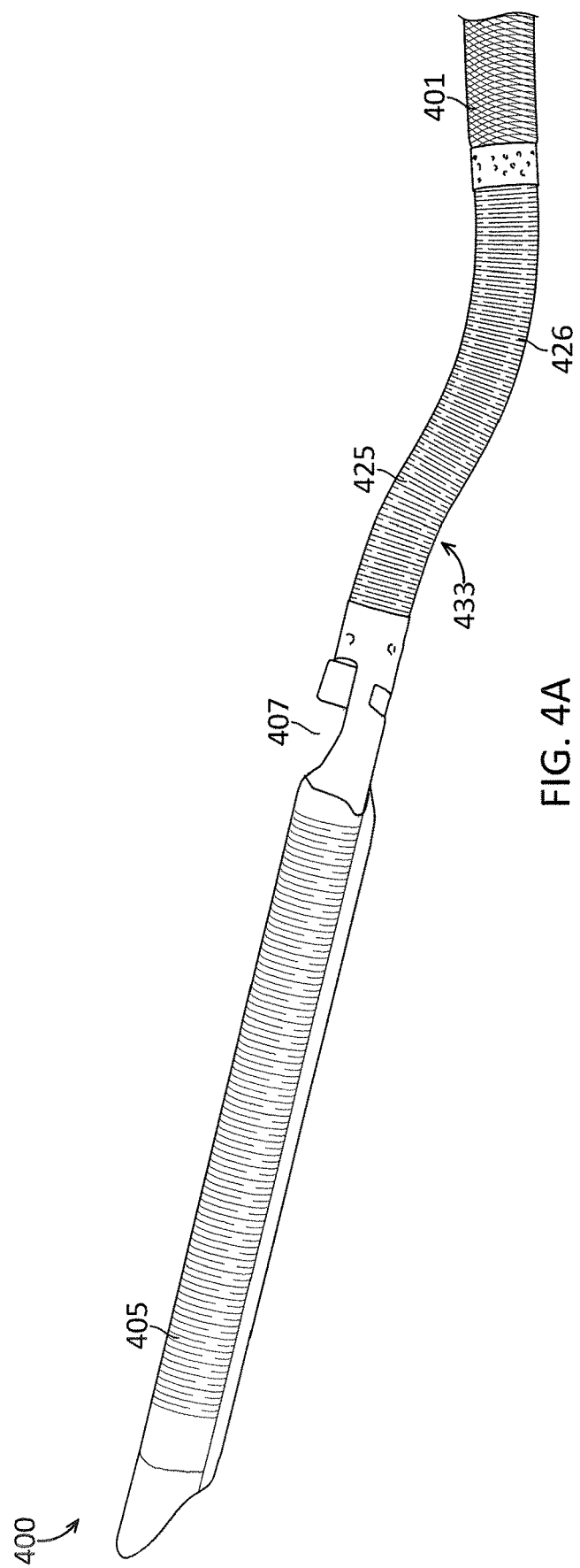
FIGS. 4A and 4B show another embodiment of an atherectomy catheter with a distal curved portion.
Figure 4B:
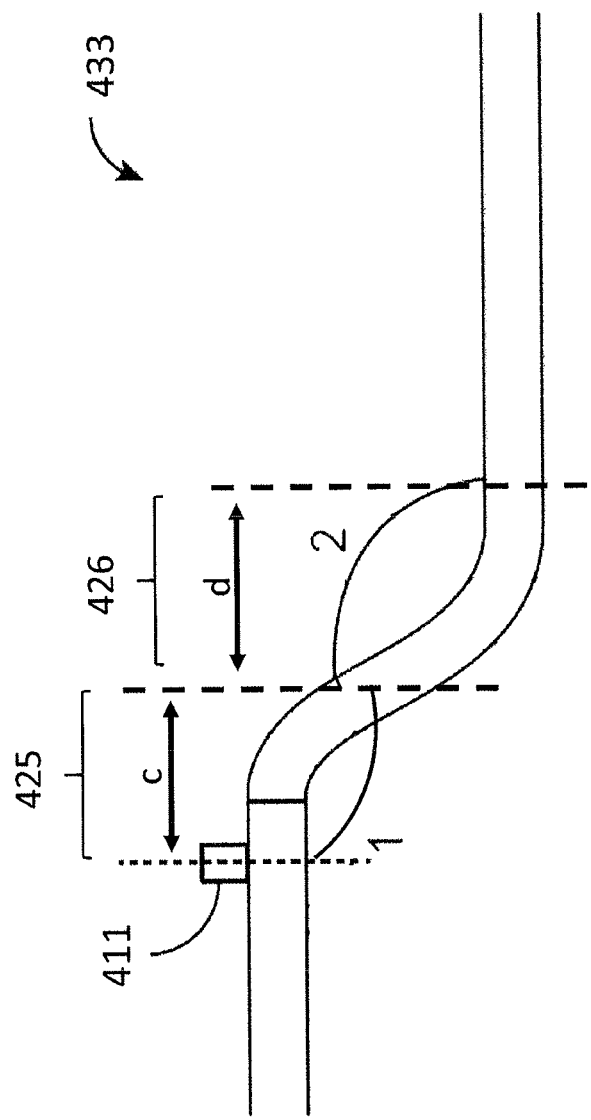

Another embodiment of an atherectomy catheter 400 including a user-activated curved portion 433 is shown in FIGS. 4A-4B. The atherectomy catheter 400 includes an elongate body 401, a nosecone 405 attached thereto, and a cutting window 407 configured to expose an annular cutter 411 therethrough. Moreover, the catheter 400 includes a curved portion 433. The curved portion 433 includes curved sections 425, 426 of opposite curvatures (i.e., one curving up and the other curving down) so as to form an approximate s-shape. In one embodiment, the s-shape can be configured such that the distal end of the catheter body 401 and/or the nosecone 405 is offset from, but substantially parallel to, a proximal end of the catheter body 401. In another embodiment, the distal end of the elongate body 401 and/or the nosecone 405 forms an angle relative to a proximal end of the catheter body 401.

Thus, as shown in FIG. 4B, the "s-shape" of the jog 433 can have a proximal curved section 426 and a distal curved section 425 having a length c. Further, there can be distal angle 1 at the distal end of the "s-shape" and a proximal angle 2 at the proximal end of the "s-shape." The lengths (c, d) and angles (1, 2) of the jog 433 can be tuned to achieve the desired jog or offset in order to obtain optimum apposition to tissue walls. For example, the angles 1 and 2 can be between 120 and 175 degrees, such as between 140 and 160 degrees. Further, in some embodiments, the length d of the proximal section 426 is greater than the length c of the distal section 425. In one example, the length c is 5 mm, the length d is 8 mm, and the angles 1 and 2 are 150 degrees for a catheter configured to be used in a vessel having a 2.5-4 mm diameter. The curved portion 433 can be a configured to adopt the s-shape during use of the catheter, as described above with respect to curved portion 333.

An exemplary user-activated curved portion 533 (e.g., for use as curved portion 433) is shown in FIGS. 5A-5D. The curved portion 533 can include a frame (e.g., made of Nitinol or stainless steel) including a series of circumferential slits 550 (e.g., laser cuts) that are patterned along the circumference of the elongate body 501 within the curved sections 525, 526. The frame of the curved sections 525, 526 can also include a longitudinal spine 560a,b, extending therethrough. The longitudinal spines 560a,b can be positioned approximately 180 degrees away from one another (i.e., on opposites sides of the elongate body 501) and extend substantially parallel to the longitudinal central axis of the elongate body 501. The frame can further include a circumferential spine 561 separating the two curved sections 525, 526. Each spine 560a,b and 561 is formed of a substantially solid piece of material that does not include slits therein. In use, as the circumferential slits 550 compress and/or overlap with one another during bending, the longitudinal spines 560a,b form the backbone of the curved sections 525, 526. Further, in some embodiments, the frame can be laminated with a layer thereover and/or under, such as a thin polymer layer, such as Tecothane. In other embodiments, the frame is not laminated to provide for greater flexibility.

Figure 5B:
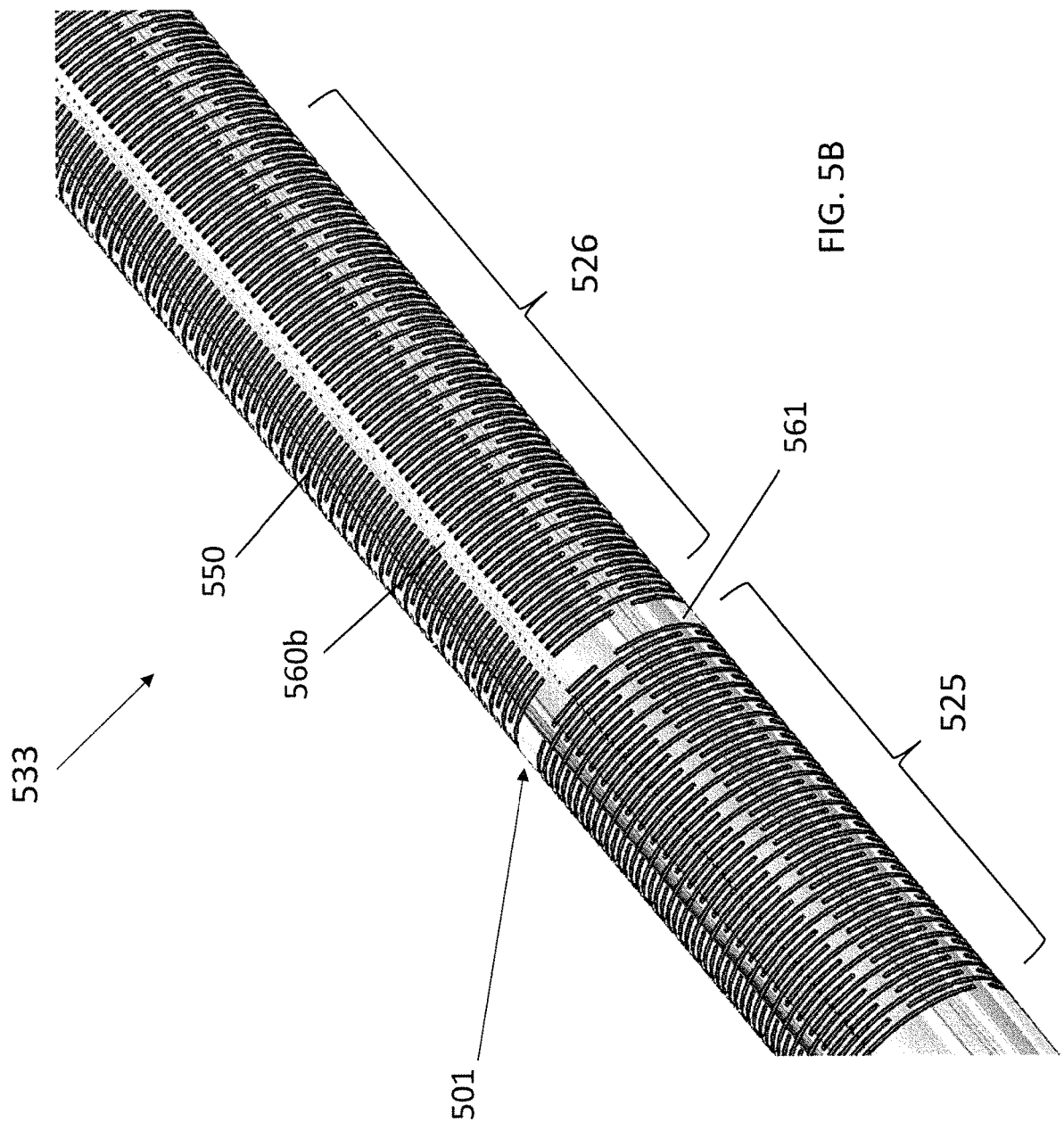
Figure 5D:
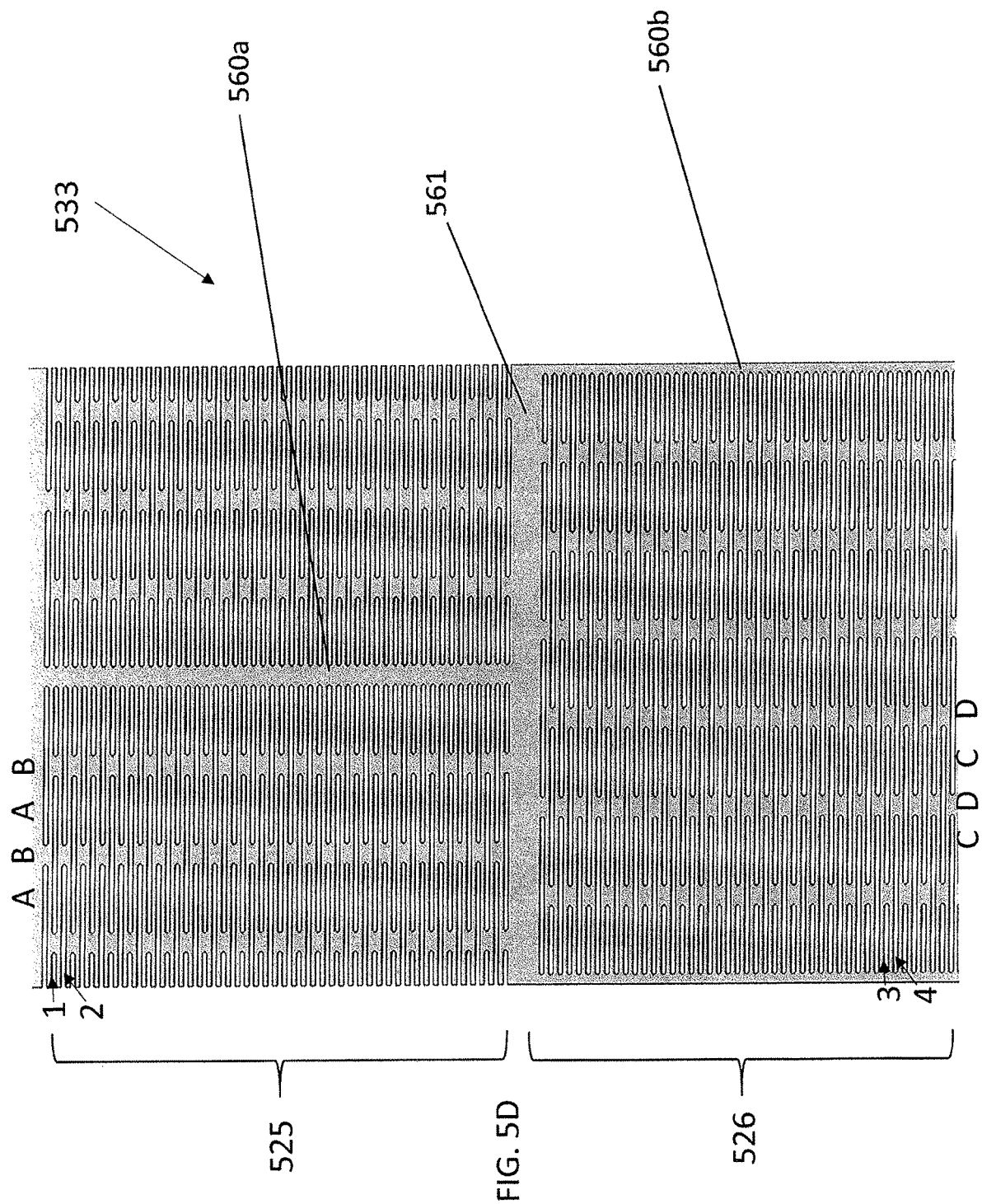
FIG. 5D is a flattened view of the curved portion of FIG. 5A.

Referring to FIG. 5D, the slits 550 can be arranged in a pattern that is configured to provide flexibility while maintaining structural integrity of the elongate body. Thus, the majority of the slits 550 can have the same length, but be offset from one another. For example, the slits in distal section 525 can be arranged in rows (1,2) and columns (A, B). Each slit 550 (except the shorter slits bordering the spine 560a) can have a length equivalent to the width of columns A+B+A. Further, the slits can be offset from one another by a distance of A+B. Thus, each column A can include slits from every row 1,2 while column B can include alternating slits (from either row 1 or 2). Column B thus provides structural integrity to the slitted portion of the device. The slits in section 526 can be similarly arranged, but can be offset such that each column C (with slits from every row 3,4) is aligned with the central axis of each column D (with slits from row 3 or 4). The offset helps provide stability to the catheter as it bends.

In some examples, pushing or pulling on a shaft of the catheter, such as the cutter drive shaft, a pullshaft, or a pullwire can activate the curved portion 533. That is, as the shaft is pulled back proximally, it can place compression on the outer elongate body 501, causing the slits 550 to compress and/or move over one another while the spines 560a,b maintain their length. The resulting s-shape (see FIG. 4B) allows the cutter (just distal to spine 460a) to be pushed up against the vessel wall.

The slits 550 shown in FIGS. 5A-5D are of a repeated, symmetrical pattern. However, the pattern need not be symmetrical. In some embodiments, the slits can all have the same length. In other embodiments, some of the slits are longer than others. In one embodiments, the slits are 0.0016" wide and 0.0575" long with a 0.0035" offset from the next row of slits.

Areas of the catheter body having a greater degree of slits will be more flexible than those having lesser degrees of slits. In one embodiment, the slits can extend all the way through the elongate catheter. In other instances, some of the slits may be deeper or shallower than others which also affects the flexibility of the corresponding region. In some variations of the curved portion, a range of deflection between the flexible segments may be achieved. This may be accomplished through different geometric patterns of slits, different spacing of the slits, frequency of the slits, size of the slits, and so forth. In some instances, the degree of stiffness may be adjusted by adding additional spines of various lengths in certain areas or adjusting the width of the spines.

Figure 6A:
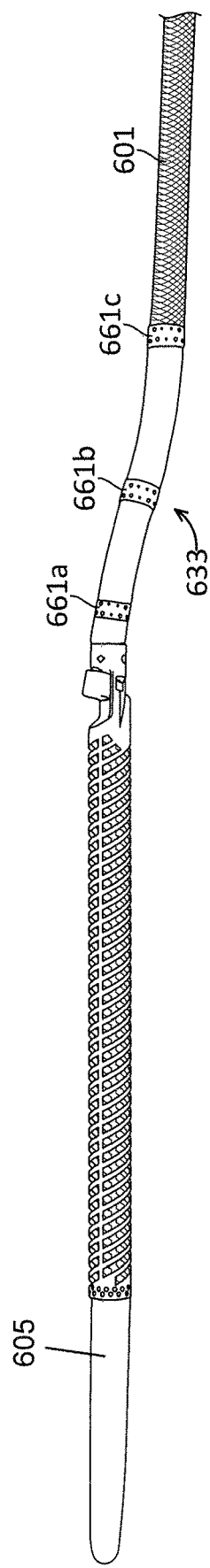
FIG. 6A shows an atherectomy catheter including another embodiment of a user-activated curved portion.
Figure 6B:
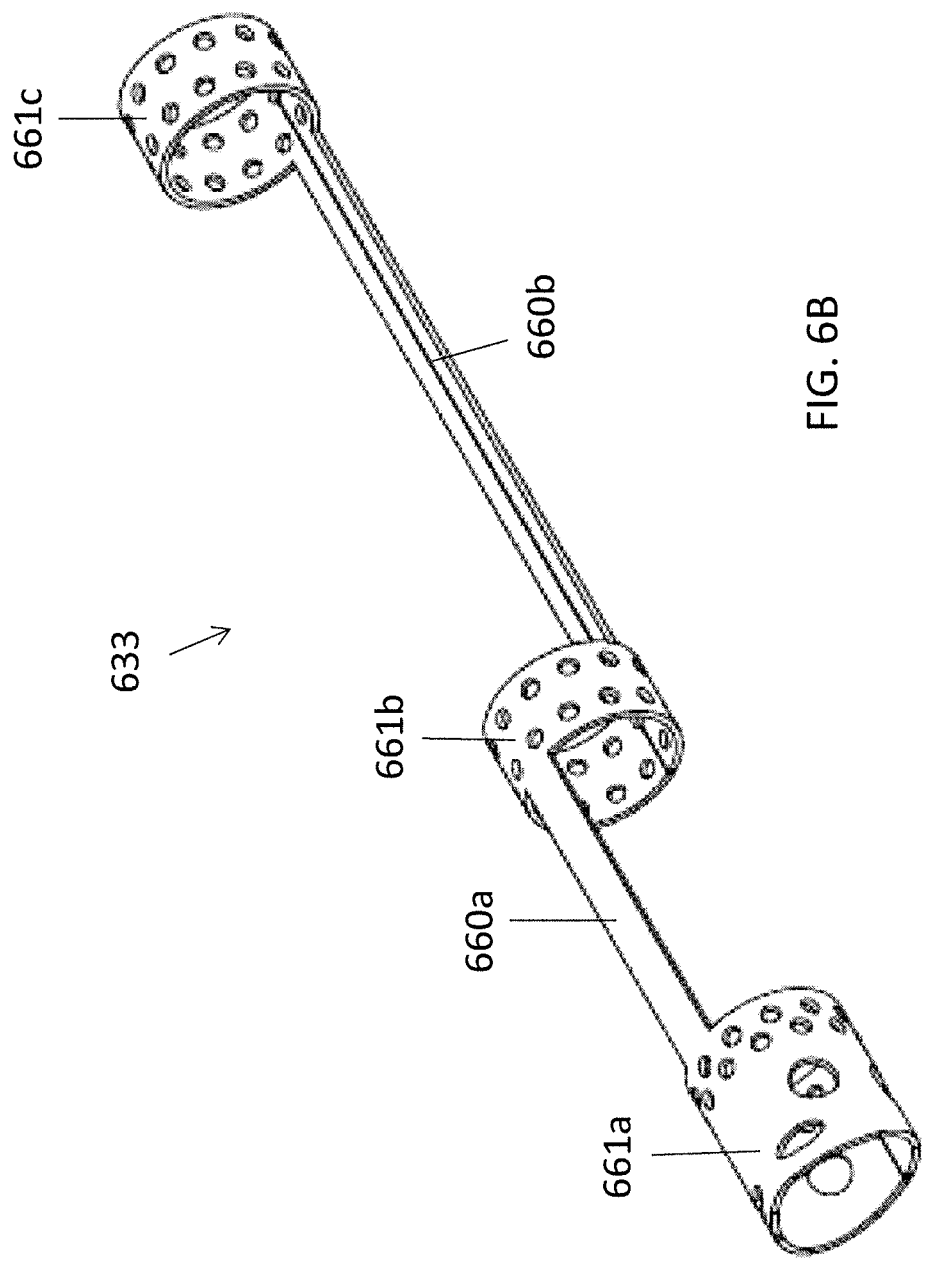
FIG. 6B shows the frame of the curved portion of FIG. 6A including annular and longitudinal spines.
Figure 6C:
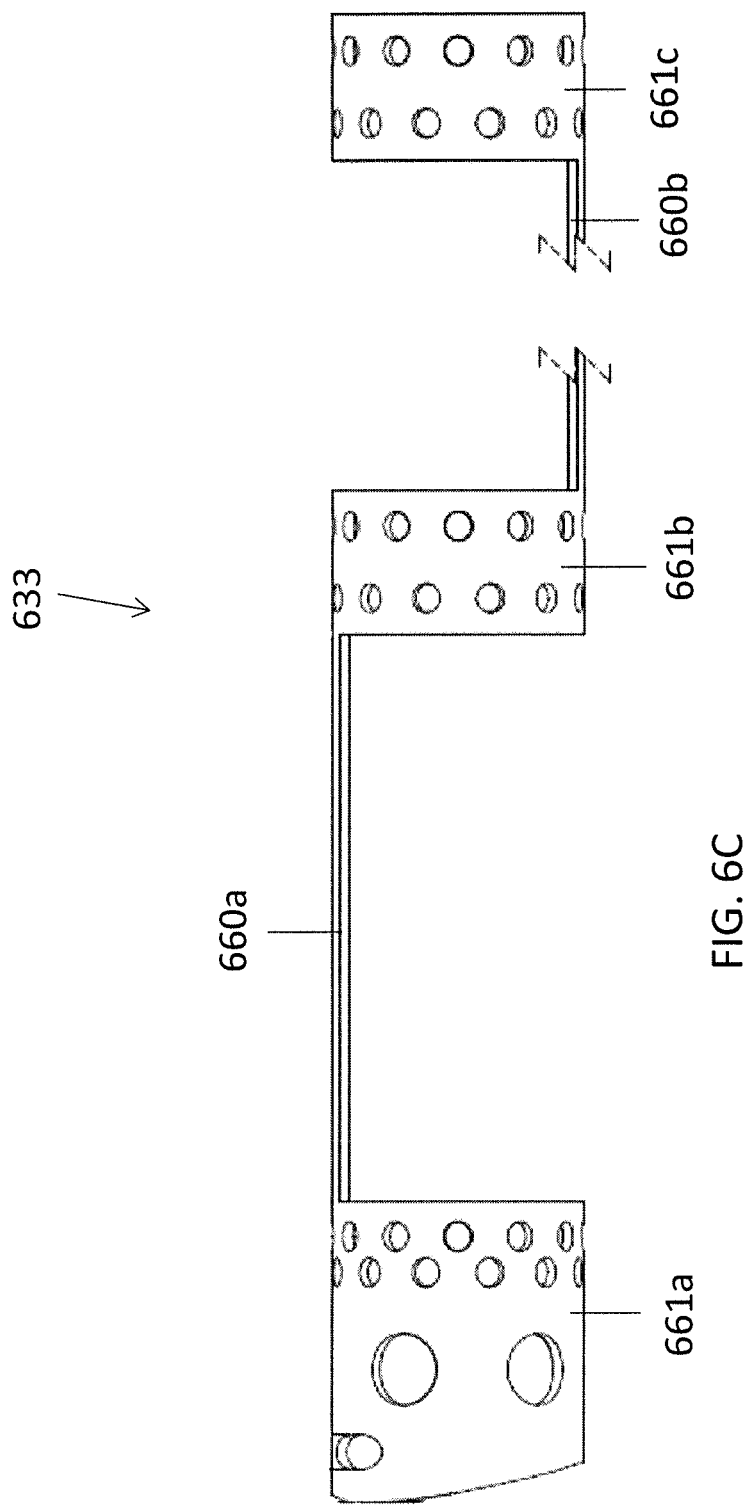
FIG. 6C shows a side view of the spine of FIG. 6B.
Figure 6D:
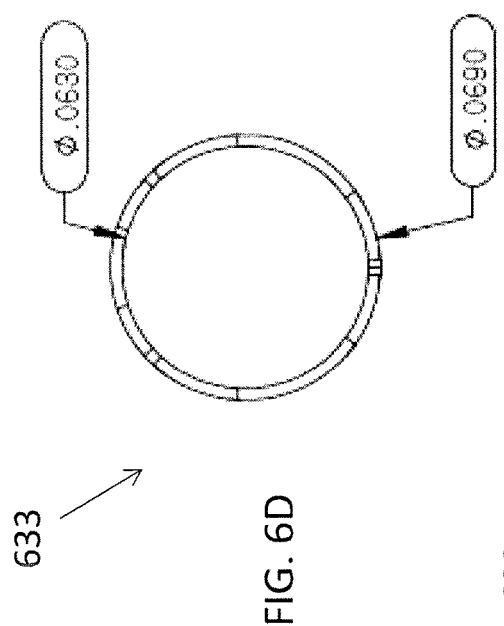
FIG. 6D shows a cross-sectional view of the spine of FIG. 6B.
Figure 6E:
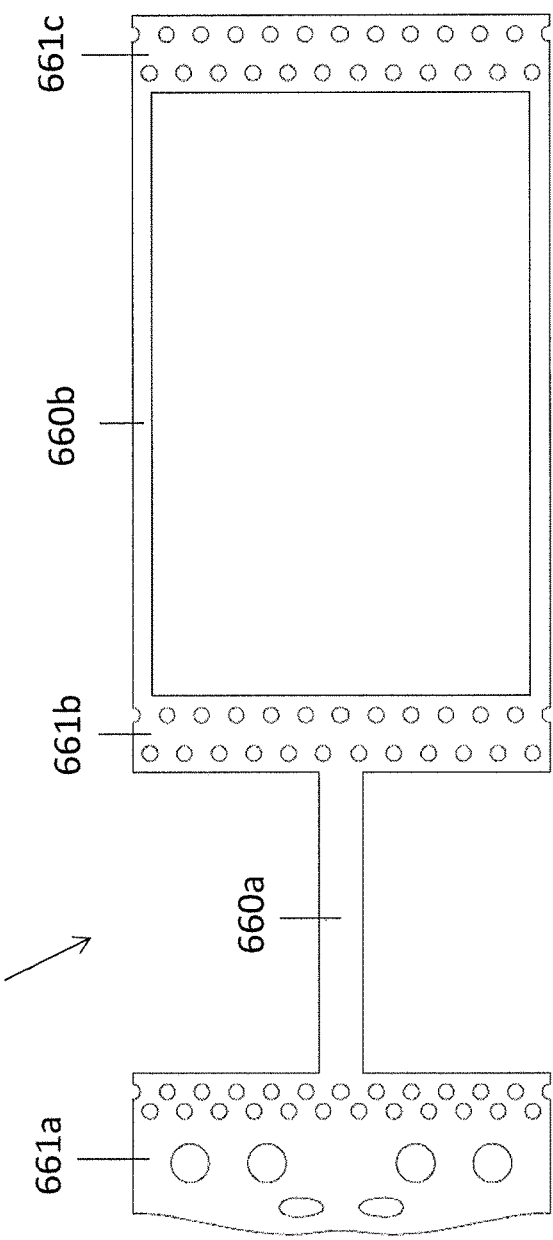
FIG. 6E is a flattened view of the spine of FIG. 6B.

Referring to FIGS. 6A-6E, another exemplary curved portion 633 (e.g., for use as curved portion 433) is shown. The curved portion 633 includes a frame having three annular ring spines 661a,b,c connected together by two longitudinal spines 660a,b. The longitudinal spines 661a,b,c can be approximately 180° away from one another. In some embodiments, the distal ring 661a,b,c can be beveled at the distal end, as shown in FIG. 6C, to allow for dropping or pivoting of the nosecone 605. Further, the space between the annular ring spines 661a,b,c and the longitudinal spines 660a,b can be open or cut-away (i.e., not include the frame material). In some embodiments, the frame can be laminated to the elongate body 601 with one or more thin polymer layers, such as Tecothane. The ring 661a,b,c can include holes therein for soldering or laminating the mechanism 633 to the elongate body of the catheter. In other embodiments, the frame can remain unlaminated to provide for greater flexibility. When compression is placed upon the mechanism 633, the mechanism 633 can bend away from each of the spines 633, forming an s-shape.

Figure 7A:
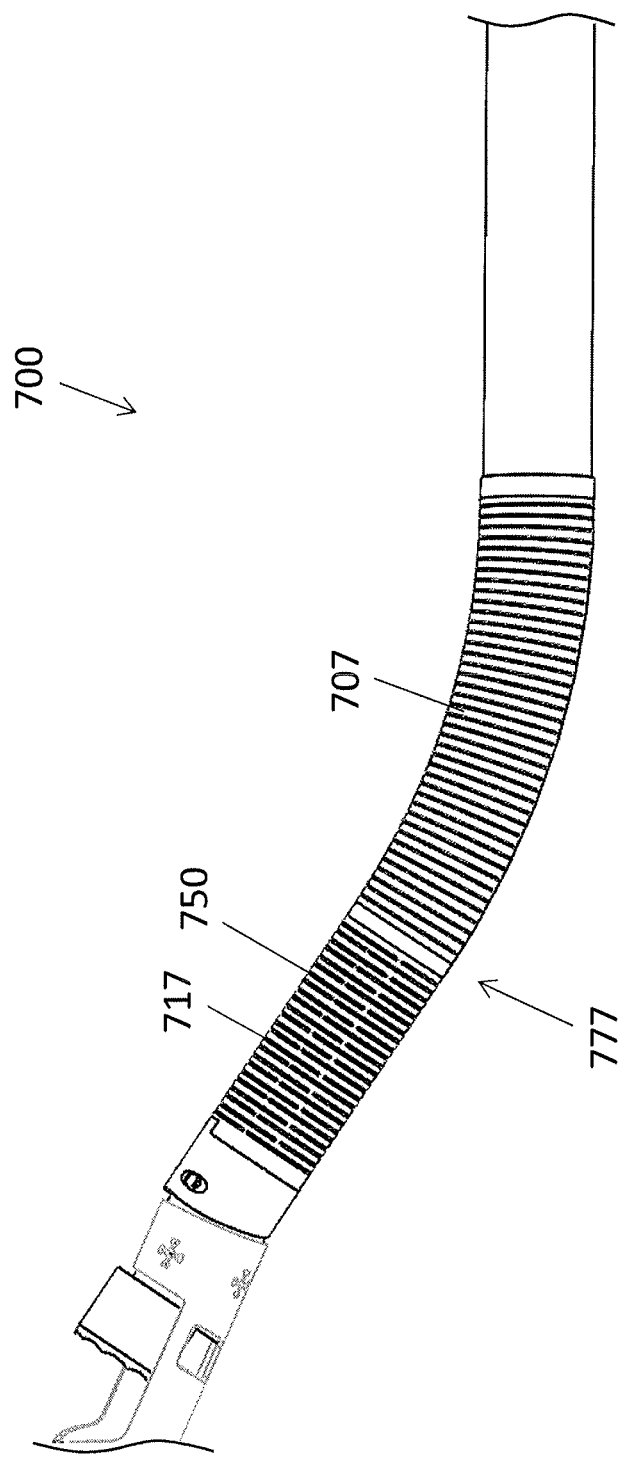
FIG. 7A shows a portion of an atherectomy catheter including a fixed jog section and a flexible section.
Figure 7B:
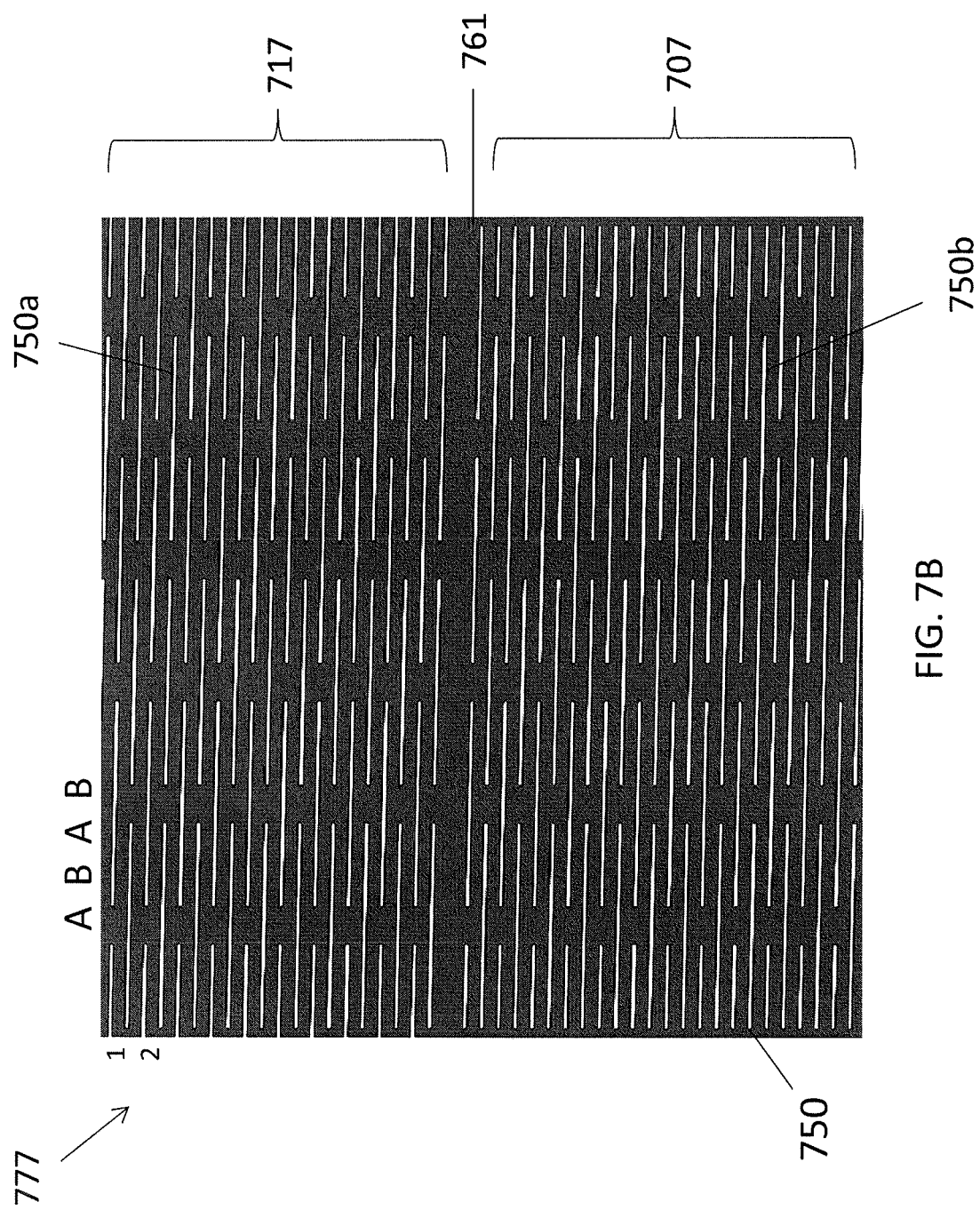
FIG. 7B shows a flattened view of the curved portion of the catheter of FIG. 7A.

Referring to FIGS. 7A and 7B, in some embodiments, an atherectomy catheter 700 can include a curved portion 777 that includes a fixed jog section 707 and a flexible section 717. The fixed jog section 707 can either be proximal to the flexible section 717 (as shown) or distal to the flexible section 717. In some embodiments, the fixed jog section 707 is longer than the flexible section 717. For example, the fixed jog section 707 can be 5-10 mm, such as 8 mm, and the flexible section 717 can be 2-6 mm, such as 5 mm. Further, in some embodiments (as shown), the fixed jog section 707 can include only a single curve rather than a double curve (e.g., forming a c-shape rather than an s-shape). The angle of the curve can be, for example, 120° to 175°, such as 130° to 160°, such as approximately 145°. The flexible section 717 can be configured to bend passively during use (i.e., when acted upon by the vessel wall), for example to form an angle of between 90° and 180°, such as 110-170°, such as 130°-160°.

In some embodiments, the curved portion 777 can be made of a laminated frame. Referring to FIG. 7B, the curved portion 777 can include a frame that includes a plurality of circumferential slits 750a,b extending therethrough. The slits 750a of the flexible section 717 can extend entirely around the circumference (i.e., include no longitudinal spine therein) while the slits 750b of the fixed jog section 707 can end at a longitudinal spine 760 extending through the fixed jog section 707. An annular spine 761 can separate the flexible section 717 and the fixed jog section 707. The frame can be made, for example, of Nitinol or stainless steel. Further, the frame can be laminated with a thin layer of polymer, such as Tecothane, on one or both sides. In some embodiments, only the fixed jog section 707 is laminated while the flexible section 717 remains unlaminated.

Referring to FIG. 7B, the slits 750a,b can be arranged in a pattern that is configured to provide flexibility in the flexible section 717 while maintaining structural integrity of the elongate body in both the flexible section 717 and the fixed jog section 707. Thus, the majority of the slits 750a,b can have the same length, but be offset from one another. For example, the slits 750a in the flexible section 717 can be arranged in rows (1,2) and columns (A, B). Each slit 750a can have a length equivalent to the width of columns A+B+A. Further, the slits can be offset from one another by a distance of A+B. Thus, each column A can include slits from every row 1,2 while column B can include alternating slits (from either row 1 or 2). Column B thus provides structural integrity to the slitted portion of the device. The slits 750a of the flexible section 717 can provide flexibility to allow the catheter 700 to achieve the desired curvature in any direction when inside the body (i.e., the slits can pull apart on the outside of the curve and compress and/or overlap when on the inside of the curve). For example, the flexible section 717 can bend to align the cutter with the edge of the vessel.

Further, the slits 750b in fixed jog section 707 (except the shorter slits bordering the spine 560a) can likewise have a length equivalent to the width of columns A+B+A. Further, the slits can be offset from one another by a distance of A+B. Thus, each column A can include slits from every row 1,2 while column B can include alternating slits (from either row 1 or 2). In fixed jog section 707, however, the spine 760 can be heat-set to set the angle of the jog, fixing the jog.

Figure 8B:
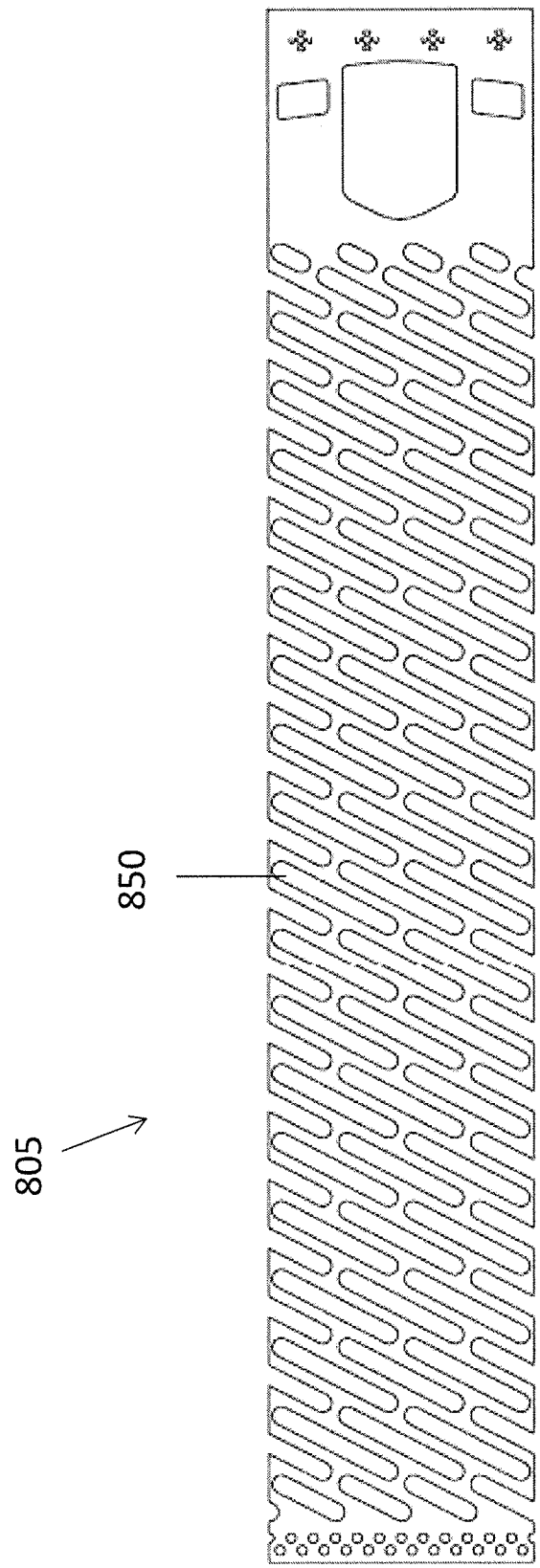
FIG. 8B shows a flattened view of a portion of the nosecone of FIG. 8A.

Referring to FIG. 8A, in some embodiments, the nosecone 805 can be flexible. That is, the elongate body can include one or more curves (as described herein), and the nosecone 805 can provide additional flexibility to allow the catheter to take the desired shape. The nosecone 805 can, for example, include a repeating laser cut pattern covered in a laminate layer. As shown in FIG. 8A, the pattern can include a series of spiral slits 850 extending around the circumference of the nosecone. some embodiments, the laser cut pattern can be cut out of stainless steal, which can be laminated with a polymer, such as Tecothane. Additional flexible nosecone designs are described in U.S. patent application Ser. No. 14/776,749, filed Sep. 15, 2015 titled "TISSUE COLLECTION DEVICE FOR CATHETER," now U.S. Patent Application Publication No. 2016-0008025-A1 and International Patent Application No. PCT/US2017/035510, filed Jun. 1, 2017 and titled "CATHETER DEVICE WITH DETACHABLE DISTAL END," both of which are incorporated by reference herein in their entireties. The flexible nosecone can be used in addition to, or in place of, any feature of the elongate body curved portions described herein.

In some embodiments, the curved portions of the elongate catheter bodies described herein can form a substantially s-shape with two different inflection points of opposite curvatures. In other embodiments, the curved portion can include a single inflection point that forms a substantially C-shape. Further, in some embodiments, one or more of the curves can be fixed. In other embodiments, one or more of the curves can be user activated (e.g., by pulling on the driveshaft or a separate pullshaft or wire). Further, any of the designs described herein can include a flexible section (e.g., of the elongate body or the nosecone) that allows the catheter to take the desired curvature during use.

In some embodiments, the amount of curvature of the user-adjusted curved portions can be further adjusted either prior to or during an atherectomy procedure based on the curvatures of the artery and the location of the plaque formation. For example, by tensioning a shaft of the catheter, the curved portion can constrict and adopt a sharper angle. Alternatively, when the shaft is relaxed, the curved portion can relax and adopt a wider angle. In such examples, the angles of deflection may be adjusted, for example, by 5 to 20 degrees.

In some embodiments, the user-adjusted curved portions can have a pre-shaped bend or curvature that can be further adjusted prior to or during an atherectomy procedure. In other embodiments, the curved portions can be straight before the user-activated bend is activated.

In any of the embodiments described herein, the nosecone can be configured to hold tissue that is debulked by the cutter. Further, the driveshaft and cutter can be configured to move distally to pack tissue into the nosecone.

In some embodiments, lamination of a framework can cause the laminating material to heat and shrink, pushing into open slits and fixing the shape of the frame (e.g., in a pre-shaped jog). For example, the curved portions 533 and/or 633 can be laminated so as to create a fixed jog that can either be further adjusted by pulling on the driveshaft or that remains fixed throughout the procedure. In other embodiments, lamination of the framework can keep the slits open and free of material, allowing for greater flexibility.

Any of the curved portions described herein may be used alone or in combination with a mechanism to deflect the nosecone. In some embodiments, the nosecone can be deflected by pulling on a cutter driveshaft. Such deflection mechanisms are described in U.S. patent application Ser. No. 15/072,272, filed Mar. 16, 2016, titled "ATHERECTOMY CATHETERS DEVICES HAVING MULTI-CHANNEL BUSHINGS," now U.S. Pat. No. 9,592,075, and U.S. patent application Ser. No. 15/076,568 filed Mar. 21, 2016, titled "ATHERECTOMY CATHETERS AND OCCLUSION CROSSING DEVICES," now U.S. Pat. No. 9,498,247, both of which are incorporated by reference in their entireties. In some embodiments, placing further tension on the drive shaft (i.e., after exposing the nosecone) can result in compression being applied to the curved portion, causing the curved portion to assume its final curved configuration. Having both the nosecone deflect and the curved portion can result in better tissue invagination and thus better or more efficient tissue cutting.

In embodiments where the nosecone is not deflected, the respective cutting windows can be optimized so as to allow for automatic invagination of tissue into the cutting window. Further, having the nosecone not deflect and relying entirely on the curved portion for tissue apposition can advantageously prevent the cutter from escaping from the nosecone during packing. Further, having the curved portion alone (i.e., without the nosecone activation) can advantageously eliminate having to use additional mechanisms to force a jog mid-surgery, such as pulling or pushing on a shaft, thereby enhancing both ease of use and enhancing image stability.

The atherectomy catheters having a curved portion described herein advantageously allows easier and closer positioning of the atherectomy cutter to plaque close to the inner artery walls. That is, the curved portions can be configured such that the exposed portion of the cutter (e.g., the area extending through the cutter window) moves closer to the vessel wall than the unexposed side of the cutter. This positioning can make cutting during the atherectomy procedure more efficient.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present.

In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An atherectomy catheter for use in a vessel comprising:
   an annular cutter; and
   an elongate catheter body including:
      a curved portion including a frame having a plurality of annular spines connected together by a longitudinal proximal spine and a longitudinal distal spine, the longitudinal proximal spine positioned approximately 180 degrees away from the longitudinal distal spine, wherein the longitudinal proximal spine and the longitudinal distal spine bend in opposite directions to give the curved portion an s-shape; and
      a nosecone attached to the elongate catheter body, the nosecone configured to pivot away from the elongate catheter body to expose the cutter, wherein an engagement surface between a distal-most annular spine of the plurality of spines and the nosecone is beveled to provide space for the nosecone to pivot.

2. The atherectomy catheter of claim 1, wherein the plurality of annular spines includes a first annular spine, a second annular spine, and a third annular spine, the longitudinal proximal spine connecting the first annular spine and the second annular spine, and the longitudinal distal spine connecting the second annular spine and the third annular spine.

3. The atherectomy catheter of claim 1, further comprising a cutting window through which the annular cutter extends, the cutting window positioned distal of curved portion and on an outer circumference of the curved portion so as to urge the cutter into the vessel.

4. The atherectomy catheter of claim 1, wherein the curved portion is configured to be activated by pulling or pushing on a shaft of the atherectomy catheter.

5. The atherectomy catheter of claim 1, further comprising at least one laminating layer positioned over or under the frame.

6. The atherectomy catheter of claim 5, wherein the at least one laminating layer is made of a polymer.

7. The atherectomy catheter of claim 1, wherein the frame is made of metal.

8. The atherectomy catheter of claim 1, wherein the distal longitudinal spine is positioned adjacent to an exposed portion of the cutter.

9. The atherectomy catheter of claim 8, wherein the distal longitudinal spine is on a same side of the elongate catheter body as the exposed portion of the cutter.

10. The atherectomy catheter of claim 1, wherein the longitudinal proximal spine forms a first angle, and wherein the longitudinal distal spine forms a second angle, the first and second angles extending in opposite directions, and wherein the first angle is between 140 and 160 degrees and the second angle is between 140 and 160 degrees.

11. The atherectomy catheter of claim 1, wherein the distal-most annular spine of the plurality of spines includes a beveled distal edge.

12. A method of performing atherectomy comprising:
   inserting an atherectomy catheter into a vessel, the atherectomy catheter including:
      an elongated catheter body, the elongated catheter body comprising a curved portion, the curved portion including a frame having a plurality of annular spines connected together by a longitudinal proximal spine and a longitudinal distal spine, the longitudinal proximal spine positioned approximately 180 degrees away from the longitudinal distal spine, wherein the longitudinal proximal spine and the longitudinal distal spine bend in opposite directions to give the curved portion an s-shape;
      an annular cutter; and
      a nosecone pivotably coupled to the elongated catheter body;
   pulling proximally on a driveshaft to pivot the nosecone with respect to the elongated catheter body and expose the cutter, wherein an engagement surface between a distal-most annular spine of the plurality of spines and the nosecone is beveled to provide space for the nosecone to pivot;
   pushing the curved portion of the elongate catheter body against a first portion of a wall of the vessel to urge the annular cutter against a second portion of the wall of the vessel; and
   rotating the annular cutter against the second portion of the wall of the vessel.

13. The method of claim 12, wherein the plurality of annular spines includes a first annular spine, a second annular spine, and a third annular spine, the longitudinal proximal spine connecting the first annular spine and the second annular spine, and the longitudinal distal spine connecting the second annular spine and the third annular spine.

14. The method of claim 12, wherein the catheter further comprises a cutting window through which the annular cutter extends, the cutting window positioned distal of the curved portion and on an outer circumference of the curved portion, the method further comprising extending the annular cutter out of the cutting window.

15. The method of claim 12, wherein activating the curved portion comprises pulling or pushing on a shaft of the atherectomy catheter.

16. The method of claim 12, wherein the distal longitudinal spine is positioned adjacent to an exposed portion of the cutter.

17. The method of claim 16, wherein the distal longitudinal spine is on a same side of the elongate catheter body as the exposed portion of the cutter.

18. The method of claim 12, wherein activating the curved portion causes the longitudinal proximal spine to form a first angle and the longitudinal distal spine to form a second angle, the first and second angles extending in opposite directions, and wherein the first angle is between 140 and 160 degrees and the second angle is between 140 and 160 degrees.

19. The method of claim 12, wherein the distal-most annular spine of the plurality of spines includes a beveled distal edge.

20. An atherectomy catheter for use in a vessel comprising:
   an elongate catheter body;
   an annular cutter; and
   a curved portion in the elongate catheter body, the curved portion including a frame having a plurality of annular spines connected together by a longitudinal proximal spine and a longitudinal distal spine, the longitudinal proximal spine positioned approximately 180 degrees away from the longitudinal distal spine, wherein the longitudinal proximal spine and the longitudinal distal spine are fixedly bent in opposite directions to give the curved portion a fixed s-shape.

21. The atherectomy catheter of claim 20, further comprising a cutting window through which the annular cutter extends, the cutting window positioned distal of the curved portion and on an outer circumference of the fixed s-shape.

22. The atherectomy catheter of claim 20, wherein the longitudinal distal spine is positioned adjacent to and on a same side of the elongate catheter body as an exposed portion of the annular cutter.

23. The atherectomy catheter of claim 20, wherein the frame is made of metal.

24. The atherectomy catheter of claim 20, wherein the longitudinal proximal spine forms a first angle, and wherein the longitudinal distal spine forms a second angle, the first and second angles extending in opposite directions, and wherein the first angle is between 140 and 160 degrees and the second angle is between 140 and 160 degrees.

25. The atherectomy catheter of claim 20, further comprising a nosecone configured to pivot away from the elongate catheter body to expose the cutter, wherein the elongate catheter body has a bevel distal edge configured to provide space for the nosecone to pivot.

26. The atherectomy catheter of claim 25, wherein a distal-most spine of the plurality of annular spines includes the beveled distal edge.

27. The atherectomy catheter of claim 20, wherein at least a portion of the frame is heat-set in the fixed s-shape.

28. The atherectomy catheter of claim 20, wherein the curved portion is laminated.

* * * * *